US012125586B2

(12) United States Patent
Feuerlein et al.

(10) Patent No.: US 12,125,586 B2
(45) Date of Patent: Oct. 22, 2024

(54) METHOD FOR THE TRANSMISSION OF PATIENT-SPECIFIC DATA TO AN EXAMINATION PROTOCOL ADJUSTMENT UNIT AND PATIENT DATA TRANSMISSION UNIT

(71) Applicant: Siemens Healthcare GmbH, Erlangen (DE)

(72) Inventors: Ute Feuerlein, Erlangen (DE); Christopher Dennl-Ortega Arrieta, Bretzfeld (DE); Marco Schuster, Heroldsbach (DE); Danilo Stitz, Erlangen (DE); Rainer Raupach, Heroldsbach (DE); Thomas Allmendinger, Forchheim (DE); Sebastian Dennert, Pommersfelden (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 872 days.

(21) Appl. No.: 16/574,750

(22) Filed: Sep. 18, 2019

(65) Prior Publication Data
US 2020/0105387 A1 Apr. 2, 2020

(30) Foreign Application Priority Data

Sep. 28, 2018 (DE) ...................... 10 2018 216 740.0

(51) Int. Cl.
G16H 40/63 (2018.01)
A61B 6/46 (2024.01)
(Continued)

(52) U.S. Cl.
CPC ............... *G16H 40/63* (2018.01); *A61B 6/46* (2013.01); *G16H 10/60* (2018.01); *A61B 6/032* (2013.01)

(58) Field of Classification Search
CPC .......... G16H 10/60; G16H 40/63; A61B 6/46; A61B 6/032; A61B 6/5258; A61B 6/5264
See application file for complete search history.

(56) References Cited

U.S. PATENT DOCUMENTS

2007/0162307 A1* 7/2007 Austin ................... G16H 10/60
715/779
2007/0176920 A1* 8/2007 Raijmakers ............ G16H 40/20
705/2

(Continued)

FOREIGN PATENT DOCUMENTS

CN 101271494 A 9/2008
CN 103445800 A 12/2013
(Continued)

OTHER PUBLICATIONS

Kaza, E., et al. "First MRI application of an active breathing coordinator." Physics in Medicine & Biology 60.4 (2015): 1681. (Year: 2015).*

(Continued)

*Primary Examiner* — Joshua B Blanchette
*Assistant Examiner* — Chance L Smith
(74) *Attorney, Agent, or Firm* — Harness, Dickey & Pierce, P.L.C.

(57) ABSTRACT

A method is for the transmission of patient-specific data to an examination log adjustment unit. In an embodiment, the method includes providing a user interface via a software application; receiving patient-specific data of a patient via the user interface, the patient-specific data being based on an input into the user interface; storing the patient-specific data received; and transmitting the patient-specific data to the examination log adjustment unit, the examination log adjust- (Continued)

ment unit being embodied to adjust an examination log for a medical imaging examination of the patient based upon the patient-specific data.

25 Claims, 3 Drawing Sheets

(51) Int. Cl.
*G16H 10/60* (2018.01)
*A61B 6/03* (2006.01)

(56) References Cited

U.S. PATENT DOCUMENTS

| | | | |
|---|---|---|---|
| 2008/0243759 A1 | 10/2008 | Martin et al. | |
| 2009/0099862 A1* | 4/2009 | Fireman | G16H 20/00 |
| | | | 705/2 |
| 2010/0145182 A1* | 6/2010 | Schmidt | G16H 30/40 |
| | | | 324/309 |
| 2011/0305376 A1* | 12/2011 | Neff | G16H 40/20 |
| | | | 382/128 |
| 2013/0320973 A1 | 12/2013 | Fenchel et al. | |
| 2014/0046675 A1* | 2/2014 | Harwood | G16H 40/20 |
| | | | 705/2 |
| 2014/0100882 A1* | 4/2014 | Hamilton | G06Q 10/06395 |
| | | | 705/3 |
| 2014/0288951 A1* | 9/2014 | Zielinski | G16H 15/00 |
| | | | 705/2 |
| 2015/0032466 A1* | 1/2015 | Vaze | G06Q 10/10 |
| | | | 705/2 |
| 2015/0339450 A1* | 11/2015 | Allen-Raffl | G16H 40/63 |
| | | | 705/2 |
| 2016/0239614 A1* | 8/2016 | Siva | G06F 16/24575 |
| 2017/0000446 A1 | 1/2017 | Brinker et al. | |
| 2017/0011192 A1* | 1/2017 | Arshad | G16H 40/20 |
| 2017/0046832 A1 | 2/2017 | Hofmann | |
| 2017/0143282 A1* | 5/2017 | Kovacs | G01G 19/50 |
| 2017/0193171 A1* | 7/2017 | Perlroth | G16H 40/20 |
| 2017/0231594 A1* | 8/2017 | Dominick | A61B 5/055 |
| | | | 600/410 |
| 2017/0236309 A1 | 8/2017 | Arens et al. | |
| 2017/0337493 A1* | 11/2017 | Paramasivan | G16H 40/20 |
| 2018/0060489 A1* | 3/2018 | Allmendinger | G16H 40/67 |
| 2019/0026128 A1* | 1/2019 | Grant | G16H 40/63 |
| 2019/0069869 A1* | 3/2019 | Soza | A61B 6/032 |

FOREIGN PATENT DOCUMENTS

| | | |
|---|---|---|
| CN | 106308797 A | 1/2017 |
| CN | 106466189 A | 3/2017 |
| DE | 102014209649 A1 | 11/2015 |
| EP | 3239873 A1 | 11/2017 |
| JP | 2017144238 A | 8/2017 |

OTHER PUBLICATIONS

German Office Action for German Application No. 10 2018 216 740.0 dated Aug. 9, 2019.

* cited by examiner

METHOD FOR THE TRANSMISSION OF PATIENT-SPECIFIC DATA TO AN EXAMINATION PROTOCOL ADJUSTMENT UNIT AND PATIENT DATA TRANSMISSION UNIT

PRIORITY STATEMENT

The present application hereby claims priority under 35 U.S.C. § 119 to German patent application number DE 102018216740.0 filed Sep. 28, 2018, the entire contents of which are hereby incorporated herein by reference.

FIELD

Embodiments of the invention generally relate to a method for the transmission of patient-specific data to an examination protocol adjustment unit and patient data transmission unit; and to a mobile data processing unit and a system, having a computed tomography device.

BACKGROUND

With the aid of various information systems, for example radiology information systems (RIS) and hospital information systems (HIS), it is possible for a large amount of information relating to the patient to be captured in paper form or electronically, in particular the weight, laboratory values, allergies etc. However, there is yet more information relating to the patient which is typically not directly captured in the conventional information systems, which could however be used to plan and parameterize a medical imaging examination in a yet more personalized and efficient manner.

Currently, the question of whether or not such patient-specific data is gathered before a medical imaging examination depends heavily on the respective clinic. The patient-specific data may, for example, be gathered by the patient being questioned by medical staff, in particular in a waiting room and/or directly at the medical imaging apparatus. If questioning takes place in the waiting room, particular care should be taken as to the privacy of the patient. If questioning takes place directly at the medical imaging apparatus, particular care should be taken as to the time during which the patient is occupying the medical imaging apparatus. Both aspects may lead to patient-specific data, which may be useful for the medical imaging examination, not being gathered.

SUMMARY

At least one embodiment of the invention enables an improved adjustment of an examination protocol for a medical imaging examination of the patient based upon the patient-specific data. Further advantageous aspects of the invention are taken into consideration in the claims.

At least one embodiment of the invention relates to a method for the transmission of patient-specific data to an examination protocol adjustment unit, wherein the method comprises:
  providing a user interface via a software application;
  receiving patient-specific data of a patient via the user interface, wherein the patient-specific data is based on an input into the user interface;
  storing the patient-specific data; and
  transmitting the patient-specific data to an examination protocol adjustment unit, the examination protocol adjustment unit being embodied to adjust an examination protocol for a medical imaging examination of the patient, in particular via a computed tomography device, based upon the patient-specific data.

At least one embodiment of the invention further relates to a patient data transmission unit, having
  a patient data transmission unit, comprising:
  a provisioning unit to provision a user interface via a software application;
  a receiving unit to receive patient-specific data of a patient via the user interface, the patient-specific data being based on an input into the user interface;
  a storage unit to store the patient-specific data; and
  a transmission unit to transmit the patient-specific data to an examination protocol adjustment unit, the examination protocol adjustment unit being embodied to adjust an examination protocol for a medical imaging examination of the patient based upon the patient-specific data.

At least one embodiment of the invention further relates to a patient data transmission unit, comprising:
  at least one processor to receive patient-specific data of a patient, via software driven user interface, the patient-specific data being based on an input into the software driven user interface;
  a memory to store the patient-specific data; and
  a transmitter to transmit the patient-specific data to an examination protocol adjustment unit, the examination protocol adjustment unit being embodied to adjust an examination protocol for a medical imaging examination of the patient based upon the patient-specific data.

At least one embodiment of the invention further relates to a mobile data processing unit, having a patient data transmission unit as per one or more of the disclosed aspects, the user interface and a computing unit for running the software application.

At least one embodiment of the invention further relates to a system, having
  a computed tomography device,
  a patient data transmission unit of one or more embodiments and
  an examination protocol adjustment unit, which is embodied to adjust an examination protocol for a medical imaging examination of a patient, in particular via the computed tomography device, based upon patient-specific data of the patient.

Furthermore, at least one embodiment of the invention further relates to a system, having
  a medical imaging apparatus,
  a patient data transmission unit of one or more embodiments and
  an examination protocol adjustment unit, which is embodied to adjust an examination protocol for a medical imaging examination of a patient, in particular via the medical imaging apparatus, based upon patient-specific data of the patient.

BRIEF DESCRIPTION OF THE DRAWINGS

The invention will be explained below based upon example embodiments with reference to the accompanying figures. The illustrations in the figures are schematic, greatly simplified and not necessarily to scale.

In the figures.

DETAILED DESCRIPTION OF THE EXAMPLE EMBODIMENTS

Figure 1:
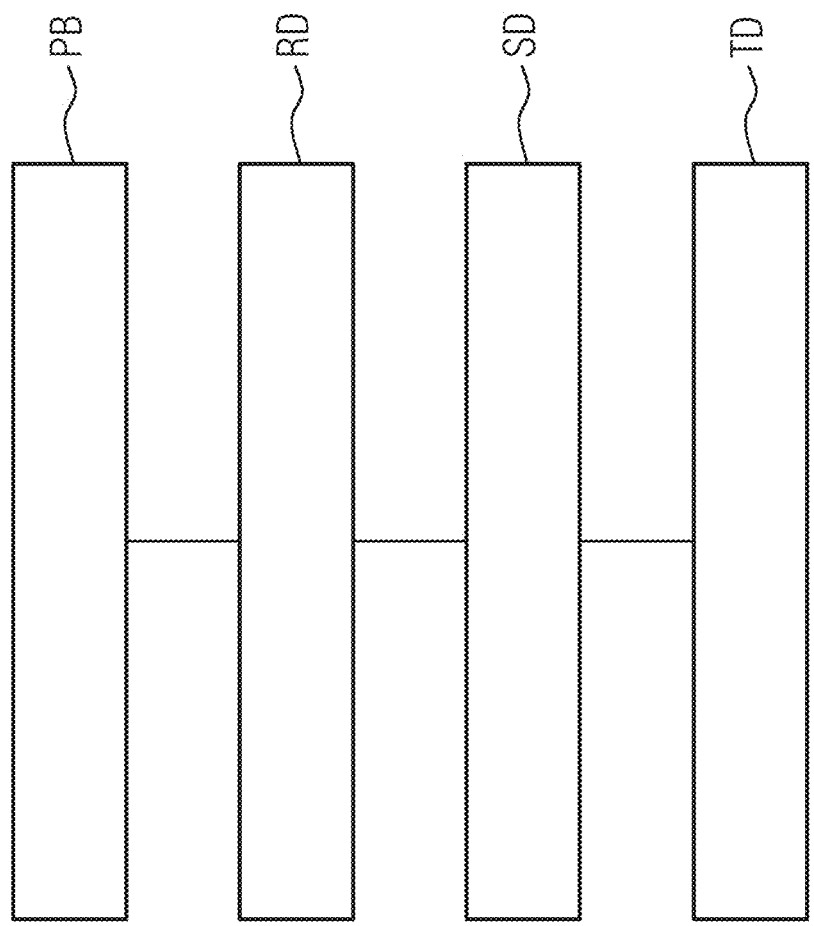
FIG. 1 shows a flow diagram for a method for the transmission of patient-specific data to an examination protocol adjustment unit.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element (s) or feature (s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C #, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (procesor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a method for the transmission of patient-specific data to an examination protocol adjustment unit, wherein the method comprises:
providing a user interface via a software application;
receiving patient-specific data of a patient via the user interface, wherein the patient-specific data is based on an input into the user interface;
storing the patient-specific data; and
transmitting the patient-specific data to an examination protocol adjustment unit, the examination protocol adjustment unit being embodied to adjust an examination protocol for a medical imaging examination of the patient, in particular via a computed tomography device, based upon the patient-specific data.

One embodiment provides that an item of examination protocol information, which relates to the examination protocol for the medical imaging examination, is received via the software application and/or that an item of patient identification information, which relates to the patient, is captured via the software application. One embodiment provides that the user interface is adjusted via the software application based upon the examination protocol information and/or based upon the patient identification information.

The term "software application" is also abbreviated by "app" in the following parts of the application. For example, the app may be used by the patient in order to input patient-specific data relating to the patient via the user interface. This may take place in the waiting room of a clinic and/or at the patient's home, for example. Via a camera, which may be integrated into a mobile data processing unit for example, it is possible to capture a photo of the patient. Based on the patient identification information, for example the photo and/or personal and/or access data of the patient, it is possible for an identification of the patient, for example via facial recognition, to be performed via the app. Depending on the identification of the patient, it is possible in particular for the user interface to be adjusted on a patient-specific basis.

The examination protocol information may, for example, relate to a body region of the patient to be examined during the medical imaging examination, one or more instructions to the patient provided during the medical imaging examination and/or examination protocol parameters of an examination protocol for the medical imaging examination.

One embodiment provides that an instruction to the patient is generated via the software application based upon the patient-specific data and/or based upon the examination protocol information. The instruction may in particular be output via the user interface. In this manner, it is possible for the patient to become acquainted with the instructions which are provided during the medical imaging examination, and/or to train the implementation thereof, in particular outside the clinic, at home for example.

One embodiment provides that the patient-specific data relates to metal on and/or in the patient and/or that the instruction to the patient relates to metal on and/or in the patient. In particular, the patient-specific data may relate to a presence and/or a position and/or a removability of the metal. In particular, the instruction to the patient may comprise an instruction to remove the metal from the patient.

The metal may in particular involve removable metal, such as rings or piercings for example. For instance, the patient may input into the user interface the body regions of the patient at which metal is present, for example that earrings are worn on the ears of the patient. Furthermore, the patient may input into the user interface whether the metal involved is removable in each case.

Based on the examination protocol information, as a function of whether the body region for which the presence of metal has been input is relevant for the medical imaging examination, it is possible for an instruction to the patient to be generated and/or output, according to which the metal is to be removed or according to which the metal can be retained. For example, it may be provided that an instruction to remove earrings is only generated and output when the examination protocol information comprises an item of information relating to the fact that a region of the head of the patient is to be examined during the medical imaging examination.

In particular, the patient may already remove the metal and/or adjust their clothing and/or their jewelry accordingly before the medical imaging examination, for example at home. For example, an instruction to the patient can be generated and/or output, according to which a belt buckle and/or rings on fingers are to be avoided. The time spent by the medical staff on determining and removing metal on the body of the patient is reduced as a result.

Furthermore, it is possible for the patient to input into the user interface which of the originally present metal parts have been removed and/or have not been removed. This patient-specific data may, for example, be transmitted to the examination protocol adjustment unit at the beginning of the medical imaging examination. In particular, based on the patient-specific data, it can be determined whether an algorithm for reducing metal artifacts in the medical imaging examination is to be used and/or which algorithm for reducing metal artifacts in the medical imaging examination is to be used. Thus, more efficient use can be made of algorithms for reducing metal artifacts.

Thus, based on the patient-specific data which has been captured with the aid of the app, it is possible to avoid a deterioration of the image quality due to metal artifacts and/or a prolonging of the examination duration, in particular caused by removable metal. Particularly if the metal is only discovered during the medical imaging examination, for example in a topogram, a considerable prolonging of the examination duration may occur. For instance, the removal of the metal from the patient, who is already positioned for the image data acquisition, may be relatively time-consuming. Furthermore, a repetition of the topogram may be required. Moreover, this may enhance the wellbeing of the patient, as a detailed questioning by medical staff, particularly in the waiting room, is not required in order to capture the patient-specific data.

One embodiment provides that the patient-specific data relates to a respiration of the patient and/or that the instruction to the patient relates to a respiration of the patient. One embodiment provides that a breathing command is output via the user interface and/or that the patient-specific data comprises a breath-holding time of the patient, for example in relation to the breathing command.

A breath-holding time can be understood in particular as meaning a duration of time during which the patient is able to deliberately avoid breathing. Patient-specific data, which relates to the respiration of the patient and/or comprises a breath-holding time, may in particular be used to avoid and/or correct motion artifacts. For instance, based on the patient-specific data, a maximum duration of a continuous image data acquisition can be determined.

Furthermore, based on the patient-specific data, it is particularly possible to automatically determine whether, and optionally which measures may be used to avoid and/or correct motion artifacts (for example a faster/increased pitch and/or a clustering of scans) and/or whether, instead of a continuous image data acquisition (one scan), two or more separate image data acquisitions (two or more scans) are to be performed. Via the examination protocol adjustment unit, the examination protocol for the medical imaging examination of the patient can be adjusted accordingly, in particular automatically.

Furthermore, based on the patient-specific data, a medical imaging apparatus can be automatically selected and/or proposed from a plurality of medical imaging apparatuses, which is optimally suitable for performing the medical imaging examination of the patient.

In particular, the breath-holding time of the patient can be captured and/or trained via the app, for example in the waiting room and/or at the patient's home. The breathing command may be generated based upon the examination protocol information, for example, and/or adjusted in an examination-specific manner. The breathing command may, for example, relate to the inspiration and/or expiration and/or information on the provided breath-holding time and/or scan time. In this manner, the patient is able to train a respiratory behavior that is most closely aligned with the medical imaging examination. Thus, time-consuming breathing command training in the clinic immediately before the medical imaging examination can be avoided. Time-consuming breathing command training is often required during cardiac examinations.

By training the respiratory behavior, in particular the breath-holding time, via the app, it is possible for the patient to hold their breath considerably longer during the medical imaging examination than without corresponding training. Motion artifacts due to breathing are thus able to be avoided.

One embodiment provides that the patient-specific data relates to an examination room for the medical imaging examination and/or examination staff for the medical imaging examination. The patient-specific data may in particular comprise information relating to a configuration of the examination room which is preferred by the patient, for example in relation to one or more colors of light, music, noises or the like. The patient-specific data may in particular comprise information relating to examination staff preferred by the patient, for example the names and/or a photo of a person, which for example may be selected by the patient via the app from a list with a plurality of people.

Based on the patient-specific data, the configuration of the medical examination room, in which the medical imaging apparatus is situated, can be adjusted and/or medical staff can be selected as examination staff for the medical imaging apparatus.

The examination room and/or the medical imaging examination can be automatically adjusted to the patient, as soon as they enter the examination room, for example by the patient being identified via an automatic facial recognition based upon a photo and/or camera image, which is recorded in the examination room and shows the patient, and by the patient-specific data, which is assigned to the patient, and/or the adjusted examination protocol, which is assigned to the patient, being loaded and/or processed.

As a result, motion artifacts can be avoided, as patients, in particular older patients and children, generally become calmer, more relaxed and cooperative due to these measures. Keeping the same examination staff can be very helpful in the case of patients, for which the medical imaging examination has to be performed multiple times, for example due to a tumor and/or due to a chronic illness, in order to achieve a high comparability between the medical imaging examinations.

One embodiment provides that the examination protocol is adjusted via the examination protocol adjustment unit based upon the patient-specific data and/or that the medical imaging examination is performed based upon the adjusted examination protocol. In particular, the examination protocol may have examination parameters. The examination parameters may, for example, relate to a scan sequence, breathing instructions, an energy and/or an intensity of an X-ray radiation, a contrast medium injection, a feed rate and/or a feed step size for a patient positioning plate, a location of an acquisition region and/or algorithms for dosage reduction, for image reconstruction, for artifact correction, and/or for image data processing.

At least one embodiment of the invention further relates to a patient data transmission unit, having
    a provisioning unit for providing a user interface via a software application,
    a receiving unit for receiving patient-specific data of a patient via the user interface, wherein the patient-specific data is based on an input into the user interface,
    a storage unit for storing the patient-specific data and
    a transmission unit for transmitting the patient-specific data to an examination protocol adjustment unit, which is embodied to adjust an examination protocol for a medical imaging examination of the patient, for example via a computed tomography device, based upon the patient-specific data.

The patient data transmission unit may, in particular, be embodied to carry out a method as per one or more of the disclosed aspects.

At least one embodiment of the invention further relates to a mobile data processing unit, having a patient data transmission unit as per one or more of the disclosed aspects, the user interface and a computing unit for running the software application.

One embodiment provides that the user interface is at least partially formed by a touch-sensitive screen of the mobile data processing unit and/or a camera of the mobile data processing unit and/or a voice interface of the mobile data processing unit. The voice interface, in particular, may be embodied as bidirectional and/or may have a microphone and/or a loudspeaker, for example. The user interface may, in particular, involve a graphical and/or voice user interface.

One embodiment provides that the mobile data processing unit is a smartphone or a tablet computer. In accordance with a further embodiment, the mobile data processing unit is a notebook or a smartwatch. The storage unit may, in particular, be a computer-readable medium, for example a memory card of the smartphone or the tablet computer. In particular, the patient-specific data and/or information, which has been determined based upon the patient-specific data, is stored locally in the mobile data processing unit.

At least one embodiment of the invention further relates to a system, having
    a computed tomography device,
    a patient data transmission unit of one or more embodiments and
    an examination protocol adjustment unit, which is embodied to adjust an examination protocol for a medical imaging examination of a patient, in particular via the computed tomography device, based upon patient-specific data of the patient.

Furthermore, at least one embodiment of the invention further relates to a system, having
    a medical imaging apparatus,
    a patient data transmission unit of one or more embodiments and
    an examination protocol adjustment unit, which is embodied to adjust an examination protocol for a medical imaging examination of a patient, in particular via the medical imaging apparatus, based upon patient-specific data of the patient.

The medical imaging examination may in particular be a computed tomography examination. The medical imaging apparatus may, for example, be chosen from the group of imaging modalities which consists of an X-ray device, a C-arm X-ray device, a computed tomography device (CT device), a molecular imaging device (MI device), a single-photon emission computed tomography device (SPECT device), a positron emission tomography device (PET device), a magnetic resonance tomography device (MR-device) and combinations thereof, in particular a PET-CT device and a PET-MR device.

The medical imaging apparatus may further have a combination of an imaging modality, which is selected from the group of imaging modalities for example, and an irradiation modality. In this context, the irradiation modality may, for example, have an irradiation unit for therapeutic irradiation.

One embodiment provides a system, further having a mobile data processing unit as per one or more of the disclosed aspects, which has the patient data transmission unit.

The solution according to at least one embodiment of the invention enables an improved adjustment of an examination protocol for a medical imaging examination based upon patient-specific data. Through use of the app, it is possible for even more patient-specific information to be made available electronically and used than was previously possible with conventional clinical information systems. The time spent by medical staff can be significantly reduced as a result. The examination can be even better adjusted to the individual requirements of the patient and the privacy of the patient can be better protected. The wellbeing and thus the willingness of the patient to cooperate can be enhanced as a result. The solution according to the invention thus enables both an impairment of the medical imaging examination due to artifacts to be reduced and also a dosage exposure of the patient to be lowered.

In the context of embodiments of the invention, features which are described in relation to different embodiments of the invention and/or different claim categories (method, use, apparatus, system, arrangement, etc.) can be combined to form further embodiments of the invention. For example, a claim relating to an apparatus can also be developed with features which are described or claimed in connection with a method, and vice versa. In this context, functional features of a method can be implemented by correspondingly embodied object components. In addition to the embodiments of the invention expressly described in this application, many further embodiments of the invention are conceivable, at which the person skilled in the art can arrive without departing from the scope of the invention, as specified by the claims.

The use of the indefinite article "a" or "an" does not preclude that the relevant feature can also be present plurally. The use of the expression "have" does not preclude that the terms linked by way of the expression "have" can be identical. For example, the medical imaging apparatus has the medical imaging apparatus. The use of the expression "unit" does not preclude that the subject matter to which the expression "unit" relates can have a plurality of components that are spatially separated from one another.

FIG. 1 shows a flow diagram for a method for the transmission of patient-specific data to an examination protocol adjustment unit, wherein the method comprises the following steps:
- Providing PB a user interface B via a software application,
- Receiving RD patient-specific data of a patient 13 via the user interface B, wherein the patient-specific data is based on an input into the user interface B,
- Storing SD the patient-specific data,
- Transmitting TD the patient-specific data to an examination protocol adjustment unit 35, which is embodied to adjust an examination protocol for a medical imaging examination of the patient 13 based upon the patient-specific data.

Figure 2:
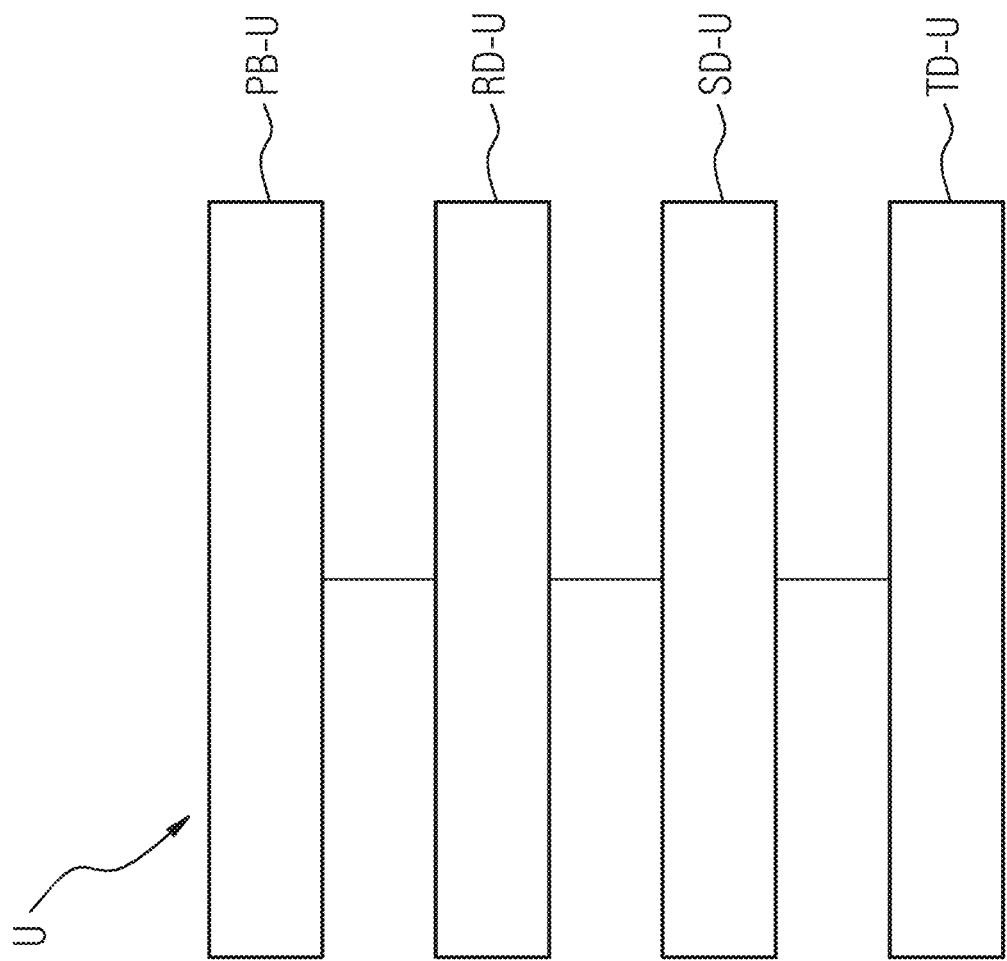
FIG. 2 shows a patient data transmission unit.

FIG. 2 shows a patient data transmission unit U, having
- a provisioning unit PB-U for providing PB a user interface B via a software application,
- a receiving unit RD-U for receiving RD patient-specific data of a patient 13 via the user interface B, wherein the patient-specific data is based on an input into the user interface B,
- a storage unit SD-U for storing SD the patient-specific data and
- a transmission unit TD-U for transmitting TD the patient-specific data to an examination protocol adjustment unit 35, which is embodied to adjust an examination protocol for a medical imaging examination of the patient 13 based upon the patient-specific data.

Figure 3:
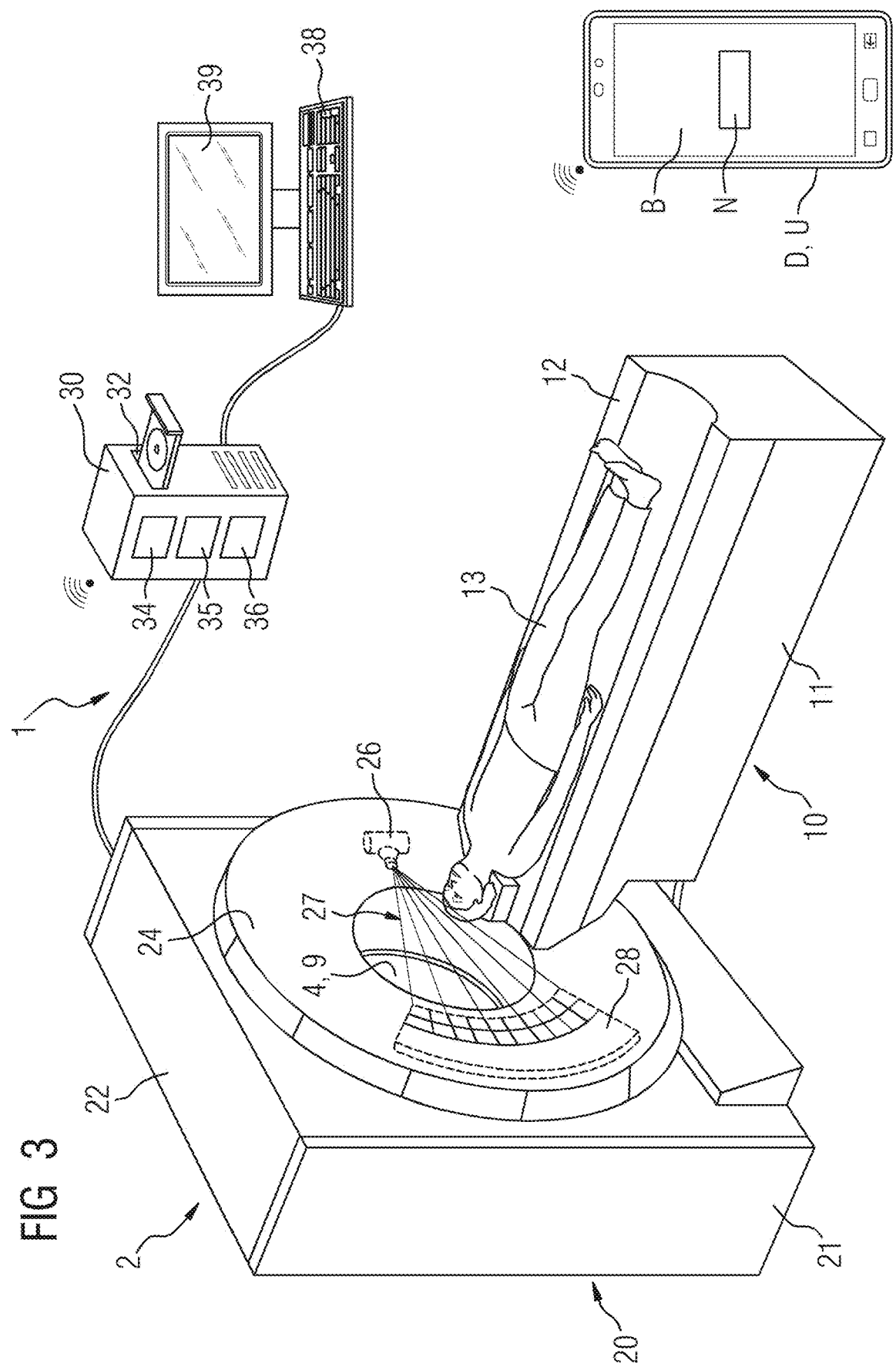
FIG. 3 shows a system comprising a computed tomography device and a mobile data processing unit.

FIG. 3 shows a system 1, having
- a computed tomography device 2,
- a mobile data processing unit D, which has the patient data transmission unit U, in the form of a smartphone,
- an examination protocol adjustment unit 35, which is embodied to adjust an examination protocol for a medical imaging examination of a patient 13 via the computed tomography device 2 based upon patient-specific data of the patient 13.

The instruction N to the patient 13 is generated via the software application based upon the patient-specific data and based upon the examination protocol information and is output via the user interface B.

The computed tomography device 2 has the gantry 20, the tunnel-shaped opening 9, the patient positioning apparatus 10 and the control apparatus 30. The gantry 20 has the stationary support frame 21, the tilting frame 22 and the rotor 24. The tilting frame 22 is arranged on the stationary support frame 21 via a tilt bearing apparatus such that it can be tilted in relation to the stationary support frame 21. The rotor 24 is arranged on the tilting frame 22 via a rotary bearing apparatus such that it can be rotated in relation to the tilting frame 22.

The patient 13 is able to be introduced into the tunnel-shaped opening 9. The acquisition region 4 is situated in the tunnel-shaped opening 9. In the acquisition region 4, a region of the patient 13 that is to be imaged is able to be positioned such that the radiation 27 can pass from the radiation source 26 to the region to be imaged and, following an interaction with the region to be imaged, can reach the radiation detector 28.

The patient positioning apparatus 10 has the positioning base 11 and the positioning table 12 for positioning the patient 13. The positioning table 12 is arranged on the positioning base 11 so as to be able to move in relation to the positioning base 11, such that the positioning table 12 is able to be introduced into the acquisition region 4 in a longitudinal direction of the positioning table 12.

The computed tomography device 2 is embodied to acquire projection data based upon an electromagnetic radiation 27 and has a projection data acquisition unit comprising the radiation source 26, e.g. an X-ray source, and the detector 28, e.g. an X-ray detector, in particular an energy-resolving X-ray detector.

The radiation source 26 is arranged on the rotor 24 and is embodied to emit a radiation 27, e.g. an X-ray radiation, with radiation quanta 27. The detector 28 is arranged on the rotor 24 and is embodied to detect the radiation quanta 27. The radiation quanta 27 are able to pass from the radiation source 26 to the region of the patient 13 that is to be imaged and, following an interaction with the region to be imaged, can strike the detector 28.

The controller apparatus 30 is embodied to receive the projection data acquired by the projection data acquisition unit. The controller apparatus 30 is embodied to control the computed tomography device 2. The controller apparatus 30 is a computer and has the examination protocol adjustment unit 35, the computer-readable medium 32 and the processor system 36. The mobile data processing unit D and the controller apparatus 30 are interconnected via a wireless network for data transmission.

The controller apparatus 30 furthermore has the imaging reconstruction facility 34. Via the imaging reconstruction facility 34, based upon the projection data, a medical image data set can be reconstructed.

The computed tomography device 2 furthermore has an input apparatus 38 and an output apparatus 39 which are each connected to the controller apparatus 30. The input apparatus 38 is embodied to input control information, e.g. image reconstruction parameters, examination parameters or the like. The output apparatus 39 is embodied, in particular, to output control information, images and/or acoustic signals.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for transmission of patient-specific data to an examination protocol adjustment unit, the method comprising:
   receiving patient-specific data of a patient via a user interface, the patient-specific data being based on an input into the user interface and including patient preferences including a selection by the patient of imaging examination staff available for an examination room;
   storing the patient-specific data;
   transmitting the patient-specific data to the examination protocol adjustment unit, the examination protocol adjustment unit being configured to adjust an examination protocol for a medical imaging examination of the patient and modify a configuration of the examination room by adjusting the imaging examination staff in the examination room based on the patient-specific data;
   generating an instruction for the patient based on the patient-specific data; and
   outputting the instruction via the user interface,
   wherein the selection by the patient of the imaging examination staff is stored for use in future medical imaging examinations.

2. The method of claim 1, further comprising at least one of:
   receiving an item of examination protocol information, relating to the examination protocol for the medical imaging examination; or
   capturing an item of patient identification information relating to the patient.

3. The method of claim 2, further comprising:
   adjusting the user interface based on at least one of the examination protocol information or the patient identification information.

4. The method of claim 2, wherein:
   the generating the instruction for the patient is further based on the examination protocol information.

5. The method of claim 2, wherein the patient identification information comprises a photograph of the patient.

6. The method of claim 5, further comprising:
   identifying the patient using facial recognition based on the photograph of the patient when the patient enters the examination room; and
   adjusting the configuration of the examination room by adjusting the imaging examination staff in the examination room based on identification of the patient when the patient enters the examination room.

7. The method of claim 1, wherein at least one of:
   the patient-specific data further includes information related to metal on or in the patient; or
   the instruction to the patient relates to metal on or in the patient.

8. The method of claim 1, wherein at least one of:
   the patient-specific data further includes information related to a respiration of the patient; or
   the instruction for the patient relates to a respiration of the patient.

9. The method of claim 1, wherein the instruction includes a breathing command.

10. The method of claim 1, wherein the modification of the configuration of the examination room further includes adjusting one or more of colors of lights, music, or noises in the examination room.

11. The method of claim 1, further comprising at least one of:
    adjusting the examination protocol via the examination protocol adjustment unit based upon the patient-specific data; or
    performing the medical imaging examination based upon the adjusted examination protocol.

12. The method of claim 1, wherein the patient-specific data includes a breath-holding time and the examination protocol adjustment unit is further configured to determine a maximum duration of a continuous image acquisition based on the patient-specific data.

13. A patient data transmission unit, comprising:
    a provisioning unit including a user interface;
    a receiving unit configured to receive patient-specific data of a patient via the user interface, the patient-specific data being based on an input into the user interface and including patient preferences including a selection by the patient of imaging examination staff available for an examination room;
    a storage unit configured to store the patient-specific data;
    a transmission unit configured to transmit the patient-specific data to an examination protocol adjustment unit, the examination protocol adjustment unit being configured to adjust an examination protocol for a medical imaging examination of the patient and modify a configuration of the examination room by adjusting the imaging examination staff in the examination room based on the patient-specific data; and
    a computing unit configured to generate an instruction for the patient based on the patient-specific data and output the instruction via the user interface,
    wherein the selection by the patient of the imaging examination staff is stored for use in future medical imaging examinations.

14. A mobile data processing unit, comprising:
    the patient data transmission unit of claim 13;
    the user interface; and
    the computing unit for running a software application.

15. The mobile data processing unit of claim 14, wherein the user interface comprises a touch-sensitive screen of at least one of the mobile data processing unit, a camera of the mobile data processing unit, or a voice interface of the mobile data processing unit.

16. The mobile data processing unit of claim 15, wherein the mobile data processing unit is a smartphone or a tablet computer.

17. The mobile data processing unit of claim 14, wherein the mobile data processing unit is a smartphone or a tablet computer.

18. A system, comprising:
    a computed tomography device;
    the mobile data processing unit of claim 14; and
    the examination protocol adjustment unit, configured to adjust the examination protocol for the medical imaging examination of the patient via the computed tomography device based on patient-specific data of the patient.

19. A system, comprising:
    a computed tomography device;
    the patient data transmission unit of claim 13; and
    the examination protocol adjustment unit, configured to adjust the examination protocol for the medical imaging examination of the patient via the computed tomography device based on patient-specific data of the patient.

20. A patient data transmission unit, comprising:
at least one processor configured to
  receive patient-specific data of a patient via a user interface,
  generate an instruction for the patient based on the patient-specific data, and
  output the instruction via the user interface, the patient-specific data being based on an input into the user interface and including patient preferences including a selection by the patient of imaging examination staff available for an examination room;
a memory configured to store the patient-specific data; and
a transmitter configured to transmit the patient-specific data to an examination protocol adjustment unit, the examination protocol adjustment unit being configured to adjust an examination protocol for a medical imaging examination of the patient and modify a configuration of the examination room by adjusting the imaging examination staff in the examination room based on the patient-specific data,
wherein the selection by the patient of the imaging examination staff is stored for use in future medical imaging examinations.

21. A mobile data processing unit, comprising:
the patient data transmission unit of claim 20.

22. The mobile data processing unit of claim 21, wherein the user interface comprises a touch-sensitive screen of at least one of the mobile data processing unit, a camera of the mobile data processing unit, or a voice interface of the mobile data processing unit.

23. The mobile data processing unit of claim 21, wherein the mobile data processing unit is a smartphone or a tablet computer.

24. A system, comprising:
a computed tomography device;
the patient data transmission unit of claim 20; and
the examination protocol adjustment unit, configured to adjust the examination protocol for the medical imaging examination of the patient via the computed tomography device based on patient-specific data of the patient.

25. A system, comprising:
a computed tomography device;
the mobile data processing unit of claim 21; and
the examination protocol adjustment unit, configured to adjust the examination protocol for the medical imaging examination of the patient via the computed tomography device based on patient-specific data of the patient.

* * * * *